United States Patent [19]

Krogsgaard-Larsen

[11] 4,301,287
[45] Nov. 17, 1981

[54] HETEROCYCLIC COMPOUNDS

[75] Inventor: Povl Krogsgaard-Larsen, Blovstrφd, Denmark

[73] Assignee: H. Lundbeck & Co. A/S, Copenhagen-Valby, Denmark

[21] Appl. No.: 104,080

[22] Filed: Dec. 17, 1979

Related U.S. Application Data

[62] Division of Ser. No. 917,118, Jun. 19, 1978.

[30] Foreign Application Priority Data

Jun. 20, 1977 [GB] United Kingdom ............... 25740/77

[51] Int. Cl.³ ......................................... C07D 491/113
[52] U.S. Cl. ..................................... 546/19; 546/220; 546/221; 546/242; 546/116; 424/256
[58] Field of Search ............... 546/242, 247, 225, 207, 546/19, 220, 221

[56] References Cited

U.S. PATENT DOCUMENTS 2,784,190  3/1957  Nathan et al. ...................... 546/242
3,186,991  6/1965  Ohnacker ........................ 546/242 X

OTHER PUBLICATIONS

Prill et al.; Jour. Amer. Chem. Soc.; 55; (1933), pp. 1233–1241.
Howton; Jour. Org. Chem.; 10(4), (1947); pp. 277–282.

Primary Examiner—Joseph Paul Brust
Attorney, Agent, or Firm—Gordon W. Hueschen

[57] ABSTRACT

The compound Ia

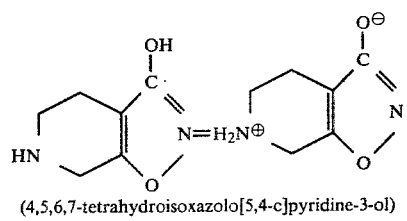

(4,5,6,7-tetrahydroisoxazolo[5,4-c]pyridine-3-ol)

has been shown to possess GABA-related activity. The invention relates to Ia and derivatives thereof, covered by the formula

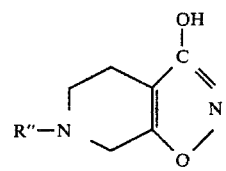

in which R" is hydrogen, acetyl or a group of the general formula VII

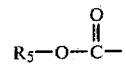

in which $R_5$ is $C_{1-8}$ alkyl; phenyl; phenyl substituted in the 4-position with halogen, lower alkoxy, or lower alkyl; or phenylalkyl in which the phenyl group may be substituted in the 4-position with halogen, lower alkoxy, or lower alkyl; and salts thereof. Novel intermediates for preparing I are

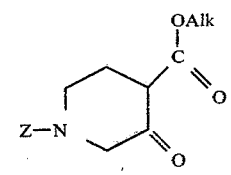

in which Alk is a lower alkyl group and Z is hydrogen or an amino-protecting group;

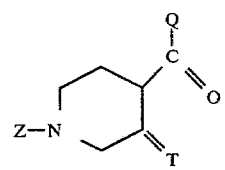

wherein Z is hydrogen or an amino-protecting group, T is a group convertible, by hydrolysis, into an oxy group, and Q is a leaving group which, on reaction with hydroxylamine, forms a hydroxamic acid group;

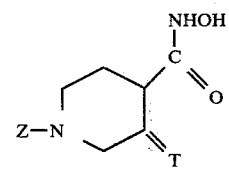

wherein Z and T are as defined above;

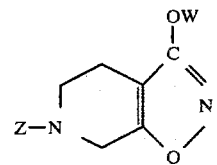

wherein Z is as defined above, and W is hydrogen or a group removable to yield the free hydroxy group, with the proviso that at least one of Z and W is different from hydrogen.

8 Claims, No Drawings

HETEROCYCLIC COMPOUNDS

This is a division of application Ser. No. 917,118, filed June 19, 1979.

The present invention relates to novel compounds having GABA-related activity.

GABA (gamma-aminobutyric acid) is known to be a neurotransmitter in the central nervous system (CNS) in mammals. GABA is found predominantly in the brain where it is a dominant inhibitory transmitter (Curtis, D. R. and Johnston, G. A. R., Ergebn. Physiol., 1974, 69, 97–188).

It has been reported (Arzneimittelforschung, 1968, 18, 311–315) that muscimol of the formula

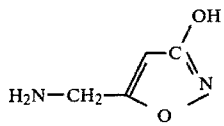

(a substance found in fly amanita (Amanita muscaria)) has various interesting pharmacological properties and especially shows an inhibition of motoric functions. Later, it was reported that muscimol is a very potent GABA agonist with respect to bicuculline-sensitive postsynaptic receptors (Johnston et al., Biochem. Pharmacol., 1968, 17, 2488, and Curtis et al., Brain Res., 1971, 32, 69–96), but it also shows activity as an inhibitor of the high affinity uptake of GABA in rat brain slices (Johnston, Psychopharmacologia, 1971, 22, 230–233). Reduced function in the GABA system is believed to be related to the etiology of parkinsonism, epilepsy, Huntington's chorea (Thomas N. Chase and Judith R. Walters, GABA in Nervous System Function, edited by E. Roberts, T. N. Chase, and D. B. Tower, Raven Press, New York, 1976, 497–513) and schizophrenia, and administration of agents influencing the GABA system is therefore under consideration and research for the therapeutical treatment of such GABA system malfunction-related diseases. It is also under consideration to administer agents influencing the GABA system against diseases in which malfunctions of the pituitary hormones are involved, e.g. diseases where a decreased secretion of prolactin is involved, and it is, furthermore, contemplated that such agents may be useful against artereoschlerotic diseases in the brain where a vasodilation is desired. However, unfortunately, muscimol has toxic effects, such as narcotic effects (derealisation and depersonalisation), and the difference between the effective dose and the toxic dose of muscimol is very small (Arzneimittelforschung, 1968, 18, 311–315), which may limit or prevent the therapeutic use of muscimol. Furthermore, it would be highly desirable to provide a substance having a more specific GABA activity than muscimol which, as mentioned above, shows considerable GABA-uptake inhibitor activity in addition to its GABA agonist activity. In an attempt to establish a structure/activity relation, various muscimol-analogues or muscimol-like substances have been synthesized and tested (P. Krogsgaard-Larsen et al., Journal of Neurochemistry, 1975, 25, 797–802 and 803–809). However, none of the compounds tested showed a GABA agonist activity of the same potency as that of muscimol.

The present invention relates to novel compounds showing GABA-related activity, to salts thereof with acids or bases, and to pharmaceutical compositions containing the novel compounds or a salt thereof as an active ingredient. Moreover, the present invention relates to methods for the preparation of the novel compounds and salts thereof and to a method for the treatment of neurological and psychiatrical disorders, such as epilepsy, parkinsonism, schizophrenia and Huntington's chorea, or diseases in which malfunctions of the pituitary hormones are involved, or artereoschlerotic diseases in the brain where a vasodilatation is desired, by administering a therapeutically active amount of the novel compound or a non-toxic salt thereof to a living animal body including human beings.

According to the present invention, it has now been found that the novel compound of the formula Ia

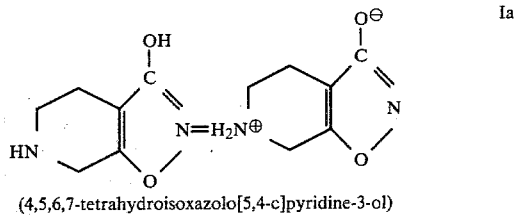

(4,5,6,7-tetrahydroisoxazolo[5,4-c]pyridine-3-ol)

is well tolerated and is a very potent GABA agonist having a very specific activity, being inactive as a GABA-uptake inhibitor. Particulars concerning the activity of this compound are given in the section "Test Results" below.

The potent, specific GABA agonist activity of the compound Ia is especially remarkable on the background of the fact that the known very closely related compounds, that is,

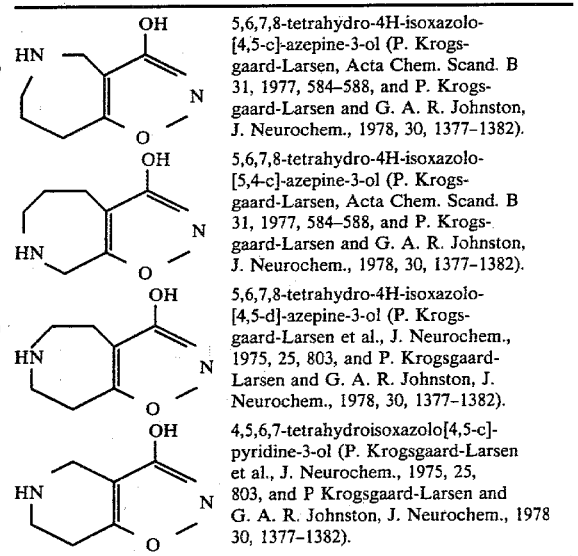

| | 5,6,7,8-tetrahydro-4H-isoxazolo-[4,5-c]-azepine-3-ol (P. Krogsgaard-Larsen, Acta Chem. Scand. B 31, 1977, 584–588, and P. Krogsgaard-Larsen and G. A. R. Johnston, J. Neurochem., 1978, 30, 1377–1382). |
| | 5,6,7,8-tetrahydro-4H-isoxazolo-[5,4-c]-azepine-3-ol (P. Krogsgaard-Larsen, Acta Chem. Scand. B 31, 1977, 584–588, and P. Krogsgaard-Larsen and G. A. R. Johnston, J. Neurochem., 1978, 30, 1377–1382). |
| | 5,6,7,8-tetrahydro-4H-isoxazolo-[4,5-d]-azepine-3-ol (P. Krogsgaard-Larsen et al., J. Neurochem., 1975, 25, 803, and P. Krogsgaard-Larsen and G. A. R. Johnston, J. Neurochem., 1978, 30, 1377–1382). |
| | 4,5,6,7-tetrahydroisoxazolo[4,5-c]-pyridine-3-ol (P. Krogsgaard-Larsen et al., J. Neurochem., 1975, 25, 803, and P Krogsgaard-Larsen and G. A. R. Johnston, J. Neurochem., 1978 30, 1377–1382). | do not show such potent and specific GABA agonist activity.

Although the present invention is not to be limited by any theory, it is believed that the remarkable selective activity of the compound Ia is ascribable to the particular position of the nitrogen atom in the 6-membered ring in relation to the acidic hydroxy group in the 5-membered ring.

The present invention therefore relates to the novel compound Ia and to derivatives thereof which upon administration will be decomposed in situ to yield the parent compound Ia, in particular compounds of the general formula I

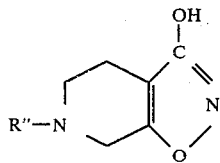

wherein R″ is hydrogen, acetyl or a group of the general formula VII

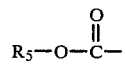

wherein $R_5$ is $C_{1-8}$ alkyl; phenyl; phenyl substituted in the 4-position with halogen, lower alkoxy, or lower alkyl; or phenylalkyl such as benzyl or phenylethyl in which the phenyl group may be substituted in the 4-position with halogen, lower alkoxy, or lower alkyl; and salts thereof.

It is believed that among the comounds I, the only species showing pronounced GABA agonist activity in the brain is the compound Ia. However, the groups R″ which are different from hydrogen may enhance the penetration of the compounds into the brain in that they may enhance the ability of the compounds to pass the blood-brain barrier, and will thereafter be split off in situ to yield the parent compound. Also, a prolonged effect of Ia may be obtained via decomposition in situ of compounds wherein R″ is different from hydrogen, to yield the parent compound.

In the present specification, "lower alkyl" and "lower alkoxy" designate such groups containing 1-4 carbon atoms.

The compounds of the general formula I may exist in a tautomeric form, as shown by the formula I′

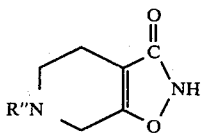

and in the present specification and claims, the formula I is to be understood as covering also this tautomeric form and mixtures of the two tautomeric forms.

Examples of compounds of the general formula I in which R″ is different from hydrogen, are:

6-acetyl-4,5,6,7-tetrahydroisoxazolo[5,4-c]pyridine-3-ol,
methyl    3-hydroxy-4,5,6,7-tetrahydroisoxazolo[5,4-c]pyridine-6-carboxylate,
ethyl 3-hydroxy-4,5,6,7-tetrahydroisoxazolo[5,4-c]pyridine-6-carboxylate,
tert.butyl    3-hydroxy-4,5,6,7-tetrahydroisoxazolo[5,4-c]pyridine-6-carboxylate,
phenyl    3-hydroxy-4,5,6,7-tetrahydroisoxazolo[5,4-c]pyridine-6-carboxylate,
4-chlorophenyl    3-hydroxy-4,5,6,7-tetrahydroisoxazolo[5,4-c]pyridine-6-carboxylate,
4-methoxyphenyl    3-hydroxy-4,5,6,7-tetrahydroisoxazolo[5,4-c]pyridine-6-carboxylate,
benzyl    3-hydroxy-4,5,6,7-tetrahydroisoxazolo[5,4-c]pyridine-6-carboxylate, and salts thereof with bases.

Examples of salts of the compound of the formula Ia are acid addition salts thereof, such as pharmaceutically acceptable salts with inorganic acids, e.g. hydrochloric, hydrobromic, nitric, sulfuric, phosphoric acids and the like, or with organic acids, such as organic carboxylic acids, e.g. acetic, propionic, glycolic, malonic, succinic, maleic, fumaric, malic, tartaric, citric, glucuronic, benzoic, pamoic acid and the like, or organic sulfonic acids, e.g. methane sulfonic, ethane sulfonic, benzene sulfonic, toluene sulfonic acid and the like, which salts may be prepared by procedures known per se, e.g. by adding the acid in question to the base, preferably in a solvent. Compounds of formula I may form pharmaceutically acceptable salts with bases, such as metal salts, e.g. sodium, potassium, calcium or aluminium salts, and ammonium and substituted ammonium salts, e.g. salts of amines such as triethylamine, triethanolamine, ethylpiperidine, procaine, dibenzylamine and the like.

TEST RESULTS

Affinity Binding Experiments

In order to study the interactions of the compound Ia with the central GABA receptors in vitro, the compound Ia was tested in affinity binding experiments. The affinity binding (sodium-independent binding) of GABA to membranes isolated from rat brains was studied as described by Enna, S. J. and Snyder, S. H., Brain Res., 1975, 100, 81–97. $IC_{50}$ values, inhibitor concentrations causing 50% inhibition of GABA binding were determined.

| Inhibitor | $IC_{50}$ value |
|---|---|
| Ia | 0.13 ± 0.005 μM* |
| Muscimol | 0.024 ± 0.003 μM |

*In earlier studies 2.6 ± 0.6 μM was found. The value stated (0.13 ± 0.005 μM) is based on studies of 5 different concentrations of Ia, each determined in triplicate, and the stated $IC_{50}$ value is calculated by log-probit analysis. The difference between the two $IC_{50}$ values determined for Ia is the result of the development of an improved technique for the preparation of rat brain membranes.

Microelectrophoretic Experiments

In order to study the interactions of the compound Ia with the central GABA receptors in vivo, the compound Ia was tested in microelectrophoretic experiments. Experiments were performed on lumbar dorsal horn interneurones and Renshaw cells of cats anaesthetized with pentobarbitone sodium. The approximate potency of the depressant actions of the compound was assessed relative to that of GABA on the basis of electrophoretic currents required to produce equal and submaximal inhibitions of the firing of the central neurones. The inhibitory action of Ia on central neurones was antagonized by the specific GABA antagonist bicuculline methochloride (BMC).

| Compound | Potency relative to that of GABA | Reversible antagonism by BMC |
|---|---|---|
| GABA | + + + | yes |
| Ia | + + + + | yes |

The compound Ia did not interact with the GABA uptake system at concentrations of $5 \times 10^4$ M, and it did not interact with the GABA metabolizing enzymes GABA:2-oxo-glutarate aminotransferase and L-glutamate 1-carboxylase at concentrations of $10^{-3}$ M.

Based on the above-mentioned experiments, the compound Ia is a specific and very potent GABA agonist.

Compound Ia has been compared with muscimol, the most potent GABA agonist so far known, in a series of pharmacological experiments:

Toxicity

Compound Ia has been shown to be a well-tolerated substance:

| Substance | Acute Toxicity (Mice) $LD_{50}$ mg/kg | | |
|---|---|---|---|
| | i.v. | i.p. | p.o. |
| Muscimol | 7 | 12 | 22 |
| Compound Ia, HBr | 80 | 145 | >320 |

Thus, compound Ia is considerably less toxic than muscimol.

Injections into Substantia Nigra in Rats (a) Bilateral injections. 0.1, 0.5, and 1.0 μg of Ia, HBr have been injected. The rats showed a pronounced stereotypic behaviour.

Ia was shown to be weaker than muscimol.

(b) Unilateral injections. 0.1 and 0.5 μg of Ia, HBr have been injected. The rats showed a strong and prolonged contralateral turning.

Ia was found to be weaker than muscimol.

Pharmacological Results in Mice (a) Potentiation of methylphenidate-induced gnawing (Scheel-Krüger et al.: Muscimol differentially facilitates stereotypy but antagonizes motility induced by dopaminergic drugs. A complex GABADOPAMINE interaction. Life Sciences, 1978, Vol. 22, 75–84).

$ED_{50}$ mg/kg (the dose which causes potentiation in 50% of the animals)
Muscimol,HBr:0.7
Compound Ia,HBr:3.0.

(b) Antagonism of morphine-induced motility (Christensen et al.: Muscimol antagonizes morphine hypermotility without potentiation of analgesia. European J. Pharmacol., 1978, 48, 459–462).

MED mg/kg (minimum effective dose)
Muscimol,HBr:0.6
Compound Ia,HBr:1.0.

(c) Antagonism of isoniazide-induced convulsions (Modification (mice, two times lower concentration of isoniazide) of Mao et al.: Evidence for an involvement of GABA in the mediation of cerebellar c-GMP decrease and the anticonvulsant action of diazepam. Naunyn-Smiedeberg's Arch. Pharmacol. 1975, 289, 369–378).

MED mg/kg (minimum effective dose)
Muscimol,HBr:0.6
Compound Ia,HBr:1.3.

Conditions and procedure for isoniazide antagonism test:

Mice, male, 20–25 g.
Isoniazide 300 mg/kg s.c.
Macrolon cages type II.

The test compound is injected i.p. in the doses 0, ½, ¼ and 1/32 of the determined "i.v. $LD_{50}$". In case of insoluble substances, the doses 0, ¼, 1/16 and 1/64 of the determined "i.p. $LD_{50}$" are used. Five mice are used for each dose level. Immediately after administration of test substance, isoniazide 300 mg/kg is injected s.c. This dose of isoniazide induces intermittent tonic clonic seizures within 60 minutes. The calculations are performed as an "on line procedure" on the EDP-terminal. The results are recorded as % increase in time until convulsions occur and in addition the least dose (MED) which shows significant effect (minimal effective dose, calculated by means of van der Waerden-test).

Conclusion

Based on these experiments, compound Ia has been shown to be a potent GABA agonist. Compound Ia is weaker than muscimol but considerably less toxic.

The compounds of formula I may be prepared by (a) subjecting a compound of the general formula V

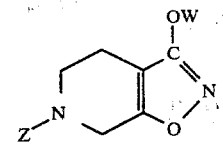

in which Z is hydrogen or an amino-protecting group readily removable, e.g. by hydrolysis, suitably a group R″ as defined above or a trityl or formyl group, and W is hydrogen or a group readily removable, e.g. by hydrolysis, to yield the free hydroxy group, such as a lower alkyl group, aralkyl, tetrahydropyranyl, acetyl, arylsulfonyl, or lower alkoxycarbonyl, with the proviso that at least one of Z and W in formula V is different from hydrogen; to removal of any group W different from hydrogen and, for the preparation of compound Ia, removal of any amino-protecting group Z, if desired, converting the compound of formula Ia obtained as a salt thereof, into the zwitterion form thereof by treatment with a base or into another salt, and, if desired, converting the compound Ia, when obtained, into a compound I in which R″ is different from hydrogen, by treatment with a reactive derivative of acetic acid or with an ester of the general formula

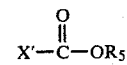

wherein X′ is a leaving group, and $R_5$ is as defined above, or (b) for the preparation of a compound of the general formula I in which R″ is different from hydrogen, subjecting a compound of the general formula IX″

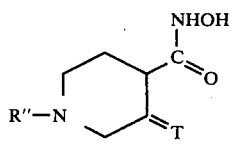

in which R" is as defined above, except hydrogen, to hydrolysis and cyclization, and if desired, converting a resulting compound in which R" is different from hydrogen, into a salt thereof.

An example of a full synthesis of the compound Ia from a known starting material appears from the examples and from the below Reaction Scheme I:

REACTION SCHEME I:

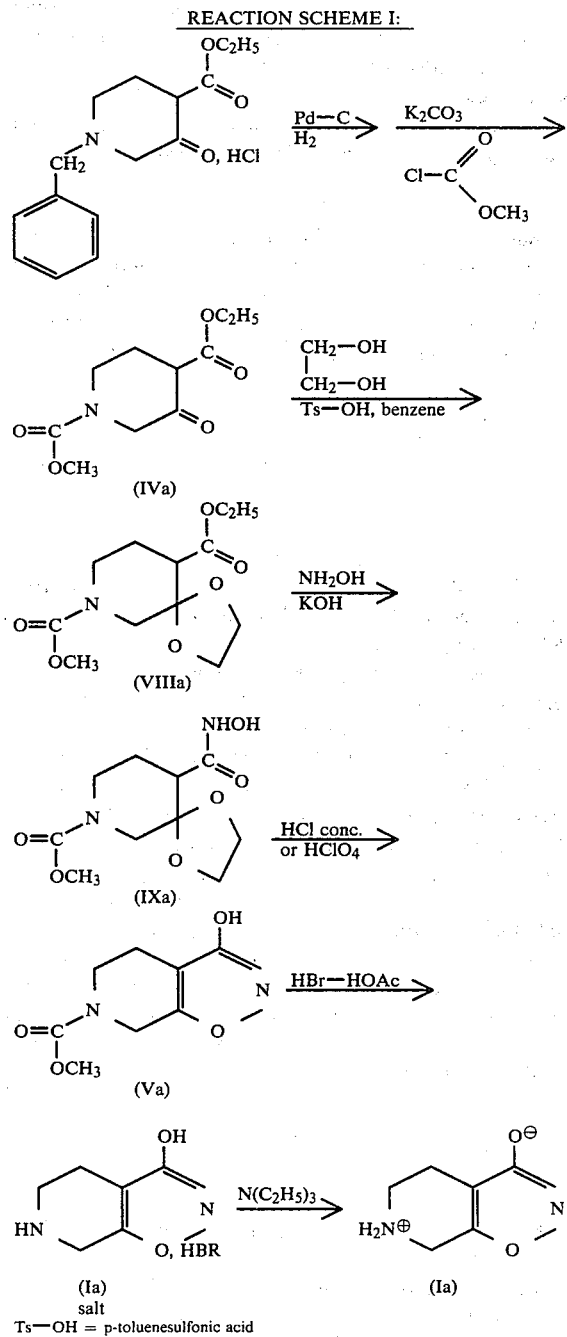

Ts—OH = p-toluenesulfonic acid

Compound IVa in reaction scheme I is a key intermediate in the above synthesis and in other syntheses of the compounds of the present invention. Similar key intermediates may contain other hydrolysable N-protecting groups and other lower alkyl groups, and hence, in its broad concept, this novel key intermediate of the present invention has the general formula IV

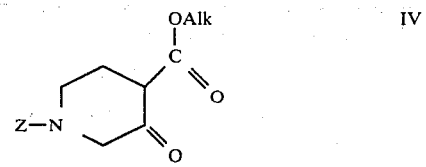

in which Alk is a lower alkyl group and Z is hydrogen or an amino-protecting group readily removable, e.g. by hydrolysis, suitably a group R" (as defined above) or a trityl or formyl group. Hence, specific examples of Z are the following: hydrogen, methoxycarbonyl, ethoxycarbonyl, propyloxycarbonyl, tert.butyloxycarbonyl, benzyloxycarbonyl, p-chlorobenzyloxycarbonyl, trityl, formyl, acetyl. Other novel intermediates according to the present invention are the compounds of the formulae VIIIa and IXa in reaction scheme I, and also the generic classes which they represent, which is, compounds of the general formula VIII'

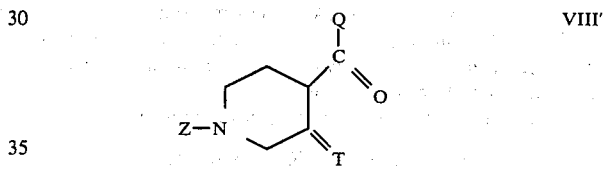

in which Z is as defined above, T is a group convertible, by hydrolysis, into an oxo group, e.g., an acetal group such as ethylene dioxy, and Q is a leaving group which, on reaction with hydroxylamine, forms a hydroxamic acid group, examples of Q being halogen, especially chlorine and bromine, hydroxy, the residue of an acid, the residue of an activated amide, the residue of an activated ester, lower alkoxy, and the like, and compounds of the general formula IX'

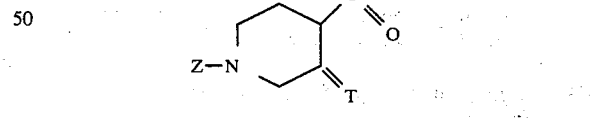

in which Z and T are as defined above, and also, at the stage of compound Va (which is both a compound of the general formula I and an intermediate for the preparation of compounds of the general formula I), an intermediate may be used which in generalized form has the formula V above.

An interesting aspect of the present invention is the compound Ia as intermediate in the preparation of compounds of formula I in which R" is different from hydrogen.

The present invention also relates to the total sequence of synthesis stages IV→VIII'→IX'→V→I and to the final stages thereof, i.e., VIII'→IX'→V→I and IX'→V→I.

The conversion of ethyl 1-benzyl-3-oxo-piperidine-4-carboxylate into the intermediate IV as exemplified by IVa, is usually performed in lower alkanols, e.g. ethanol or ethanol/water. The removal of the N-benzyl group may be effected with gaseous hydrogen in the presence of a hydrogenation catalyst, e.g. platinum, palladium or Raney nickel. The alkyl 3-oxo-piperidine-4-carboxylate formed is dissolved, e.g. in water, and treated with an acid acceptor, e.g. alkali carbonate, and an ester of chloroformic acid, e.g. methyl chloroformate. The temperature is kept near 0° C. during the reaction. The compound IV is isolated by extraction into an organic solvent followed by evaporation of the solvent.

The formation of the compound of formula VIII' as exemplified by the ethylene acetal VIIIa is usually performed in a solvent, e.g. benzene, which forms an azeotropic mixture with water. The reaction is preferably carried out at reflux temperature and with a strong acid, e.g. a sulfonic acid as catalyst.

The hydroxamic acid IX' as exemplified by IXa is synthesized by reacting VIIIa with hydroxylamine, preferably in water or a lower alcohol, e.g. methanol and usually at a temperature between −20° C. and room temperature, preferably at 0°–10° C. The compound may be isolated and purified by a manner known per se, e.g. column chromatography. When Q in formula VIII' is a halogen or the residue of an acid, the reaction is effected in the presence of a base. Alternatively, the piperidine carboxylic acid itself (VIII', Q=OH) may be reacted with hydroxylamine in the presence of a condensing agent, e.g. dicyclohexyl carbodiimide or carbonyldiimidazole. As solvent, an inert solvent, e.g. methylene chloride or chloroform can be used.

The hydrolysis of the acetal group of IXa or, quite generally, the conversion of T in compounds of formula IX' into an oxo group, followed by cyclization to a compound of formula V as exemplified by Va may be effected by an aqueous solution of a strong acid optionally also containing acetic acid, e.g. concentrated hydrochloric acid or 70% perchloric acid at a temperature between 0° C. and 100° C., preferably at 50°–80° C. The compound V may be isolated by extraction with an organic solvent or by evaporation of the water. The compound can be purified by column chromatography or by crystallization.

Removal of the protecting group Z and/or W in compound V may be effected with a strong inorganic acid, e.g. hydrochloric or hydrobromic acid, in a solvent, e.g. glacial acetic acid or water, or a mixture of water and glacial acetic acid. The temperature may be kept between room temperature and the boiling point of the solvent. The reaction time is usually short, e.g. less than 1 hour. The Ia salt may be isolated by evaporation of the solvent. The Ia salt may be transformed into Ia by treatment with a base, e.g. a tertiary amine, in a solvent, usually a mixture of water and a lower alkanol.

Compound Ia may be transformed into another salt as described above.

An interesting synthesis is illustrated in the below reaction scheme II in which a compound of the general formula I, as exemplified by the compound Ia, is prepared:

REACTION SCHEME II:

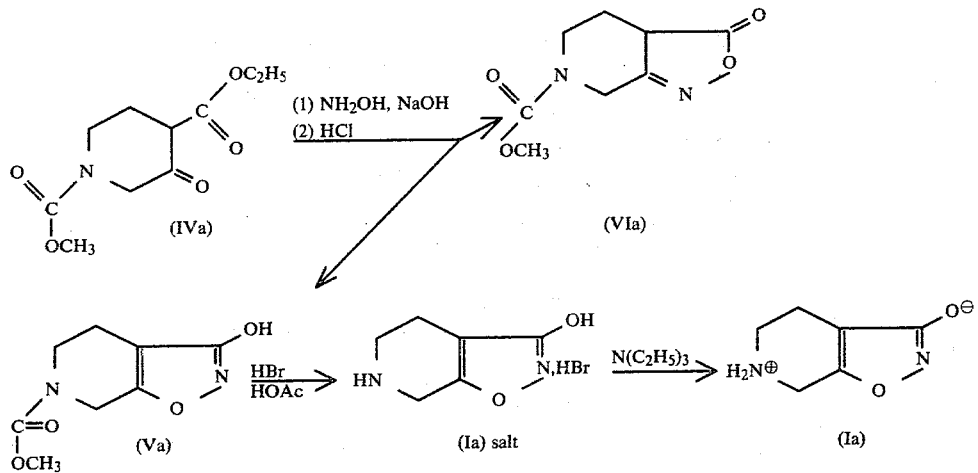

The reaction of a compound of the general formula IV as exemplified by IVa with hydroxylamine may give a mixture of a compound of the general formula V and the corresponding isomeric compound V as exemplified by Va and VIa. The reaction may be effected at a temperature between −30° C. and 50° C., preferably between −30° and −10° C. The solvent is usually water or a lower alkanol or mixtures thereof.

The process illustrated in reaction scheme II, although yielding a mixture of two isomers, is nevertheless advantageous. It is very time-saving in that it avoids the protection of the oxo group in compounds of the general formula IV and the subsequent hydroxamic acid formation. The compounds formed in the reaction of IV with hydroxylamine, as exemplified by Va and VIa, are easily separated by manners known per se, e.g. by column chromatography.

When it is desired to prepare compounds of the general formula I in which R" is different from hydrogen, one may either omit the removal of the group Z if the group Z has the same identity as the desired group R", or one may introduce such group R" into the compound of the general formula Ia.

The introduction of the group R" may be performed by manners known per se. Thus, for example, when R" is a group of the above formula VII, the introduction may be performed by treatment of compound Ia with the appropriate formic acid ester of the general formula

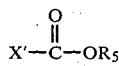

wherein X' is a leaving group, especially halogen, azido, etc., in the presence of an acid acceptor, for example an alkali carbonate. For example, the BOC-derivative can be made by means of tert.butyl azidoformate. When R" is acetyl, a reactive derivative of acetic acid, e.g. acetyl chloride or acetanhydride may be used for the introduction of the group R".

The compounds of the formula I, and salts thereof may be formulated for administration in any convenient way by analogy with other pharmaceuticals.

Thus, the composition comprising the compounds of the invention may be in the form of pharmaceutical preparations, e.g. in solid, semisolid or liquid form, which contain the active compound of the invention in admixture with a pharmaceutical organic or inorganic carrier or excipient suitable for enteral or parenteral application. The active ingredient may, e.g., be formulated with the usual carriers for tablets, pellets, capsules, suppositories, solutions, emulsions, aqueous suspensions and other suitable administration forms. Examples of carriers are glucose, lactose, gum acacia, gelatin, mannitol, starch paste, magnesium trisilicate, talc, corn starch, keratin, colloidal silica, potato starch, urea, and other carriers suitable for use in manufacturing compositions in solid, semisolid, or liquid form, and in addition auxiliary, stabilizing, thickening, colouring, flavouring, and preservative agents can be contained in the composition of this invention.

The active compound is included in the compositions of the invention in an amount sufficient to produce the desired therapeutical effect upon administration. The dosage or therapeutically effective quantity of the compound varies and also depends upon the age and condition of each individual patient being treated.

A preferred tablet or capsule formulation for oral administration contains 0.1–200 mg, preferably 1–100, especially 5–50, mg of a compound of the formula I or a salt thereof per unit dosage which may be administered 1–4 times per day or as a sustained release composition.

Injection preparations preferably contain 0.1–200 mg, preferably 1–100, especially 5–50, mg of a compound of the formula I or a salt thereof per unit dosage. A preferred injected dose is about 0.5 to 2 ml.

The invention also relates to the use of the compounds of the general formula I and salts thereof in medicaments for treating GABA system malfunction-related diseases, and a process of treating GABA system malfunction-related diseases in human beings by administering, to the human being, an effective dose of a compound of the general formula I, or a salt thereof.

In the above-mentioned compositions and the above-mentioned uses, it may be suitable or preferred to combine the compounds of the general formula I or a salt thereof with minor tranquillizers such as benzodiazepines or neuroleptics, for example butyrophenones such as haloperidol, phenothiazines such as chloropromazine, thioxanthene, and the like. In such combinations, compositions and combined usages, the neuroleptics are suitably administered in their effective amounts or, in a preferred embodiment in lower amounts than the amounts in which they would be effective when used alone.

The invention is further illustrated by the below working examples. All compounds prepared according to the working examples have been subjected to elemental analysis for C, H, N and halogen, when present, and all agreed within ±0.3% with the calculated values.

EXAMPLE 1

(Reaction scheme I)

(a) Ethyl 1-methoxycarbonyl-3-oxopiperidine-4-carboxylate (IVa)

A solution of ethyl 1-benzyl-3-oxopiperidine-4-carboxylate (Iselin, B. M. and Hoffmann, K., Helv. Chim. Acta, 1954, 37, 178) (14.0 g; 47 mmol) in aqueous ethanol (300 ml; 50%) was hydrogenated (ca. 300 kPa) in a PARR hydrogenation apparatus by using a 10% Pd-C catalyst (1.4 g). The reaction mixture was filtered and evaporated to dryness in vacuo. To an ice cooled solution of the residue in water (50 ml) was added with stirring an iced solution of potassium carbonate (19.4 g; 140 mmol) in water (20 ml) followed by addition of methyl chloroformate (11.3 g; 120 mmol). Stirring was continued at 0° C. for 30 minutes and at 25° C. for 30 minutes. The mixture was extracted with three 100 ml portions of ether. The combined and dried ($Na_2SO_4$) ether phases were evaporated in vacuo to give 10.0 g of crude product. Ball-tube distillation at 40–130 Pa (oven temperature 170° C.) gave IVa (9.0 g; 84%) as a colourless oil, which slowly crystallized, m.p. 36°–38° C. IR (film): 2980–2850 (several bands, m-s), 1700 (s), 1655 (s), 1620 (m) $cm^{-1}$. $^1H$ NMR ($CCl_4$): $\delta 12.3$ (1 H, s), 4.13 (q, J 7 Hz) and 4.0–3.9 (m) (a total of 4 H), 3,62 (3 H, s), 3,43 (2 H, t, J 6 Hz), 2.4–2.1 (2 H, m), 1.30 (3 H, t, J 7 Hz).

(b) Ethyl 1-methoxycarbonyl-3-oxopiperidine-4-carboxylate ethylene acetal (VIIIa)

A mixture of ethyl 1-methoxycarbonyl-3-oxopiperidine-4-carboxylate (9.0 g; 39 mmol), ethylene glycol (100 ml), 4-toluenesulfonic acid (0.7 g), and benzene (500 ml) was refluxed for 6 days using a Dean-Stark water separator. The mixture was washed with aqueous sodium carbonate (300 ml; 1 M), water (300 ml), and saturated aqueous sodium chloride (300 ml). The organic phase was dried ($K_2CO_3$) and evaporated in vacuo to give 8.6 g of an oil. CC [silica gel (Woelm 0.063–0.1 mm): 350 g; eluents: methylene chloride to which ethyl acetate (20–35%) was added] followed by ball-tube distillation at 40 Pa (oven temperature 170° C.) gave VIIIa (7.0 g; 65%) as a colourless oil. IR (film): 2970 (s), 2900 (s), 1730 (s) $cm^{-1}$. $^1H$ NMR ($CCl_4$): $\delta 4.05$ (q, J 7 Hz) and 3.92 (s) (a total of 6 H), 3.60 (s) and 3.7–3.0 (m) (a total of 7 H), 2.8–2.5 (1 H, t), 2.2–1.6 (2 H, m), 1.23 (3 H, t, J 7 Hz).

(c) 1-Methoxycarbonyl-3-oxopiperidine-4-carbohydroxamic acid ethylene acetal (IXa)

To a stirred and iced solution of potassium hydroxide (7.3 g; 130 mmol) in methanol (30 ml) was added hydroxylammonium chloride (6.9 g; 100 mmol). After stirring at 0° C. for further 30 minutes a solution of ethyl 1-methoxycarbonyl-3-oxopiperidine-4-carboxylate ethylene acetal (6.8 g; 25 mmol) in methanol (20 ml) was added, and the mixture was left at 8° C. for 8 days. Upon addition of glacial acetic acid (15 ml) and filtration the filtrate was evaporated in vacuo to give a treacly mass. CC [silica gel (Woelm 0.063–0.1 mm): 250 g; eluents: ethyl acetate to which methanol (15–26%) and formic acid (1%) was added] afforded IXa (1.9 g; 29%) as a crystalline and TLC-pure substance [$R_F$: 0.23; eluent: ethyl acetate-methanol-formic acid (90:9:1)]. An analytical sample was recrystallized (ethanol-benzene) to give IXa as colourless crystals, m.p. 150.0°–152.0° C. IR (KBr): 3700–3350 (m), 3280 (m), 3210 (s), 3055 (w), 3000–2870 (several bands, w-m), 1690 (s), 1640 (s), 1550 (w) cm$^{-1}$. $^1$H NMR [CDCl$_3$-DMSO-d$_6$ (1:1): $\delta$10.5–10.1 (1 H, m), 4.9–4.3 (1 H, m), 3.93 (s), 3.60 (s), and 4.1–3.1 (m) (a total of 11 H), 2.8–2.6 (1 H, m), 2.2–1.8 (2 H, m).

(d) Methyl 3-hydroxy-4,5,6,7-tetrahydroisoxazolo[5,4-c]pyridine-6-carboxylate (Va)

A solution of 1-methoxycarbonyl-3-oxopiperidine-4-carbohydroxamic acid ethylene acetal (750 mg; 2.9 mmol) in concentrated hydrochloric acid (13 ml) was heated to 70° C. for 10 minutes. The mixture was evaporated in vacuo to give a black oil. CC [silica gel (Woelm 0.063–0.1 mm): 60 g; eluents: benzene to which ethyl acetate (40–70%) and formic acid (1%) was added] gave crystalline and TLC-pure Va (244 mg; 43%) [$R_F$: 0.27; eluent: benzene-ethyl acetate-formic acid (50:50:1)]. An analytical sample was recrystallized (benzene-cyclohexane) to give pure Va as colourless crystals, m.p. 136.0°–138.0° C. IR (KBr): 3700–3300 (m), 3300–2500 (several bands, w-m), 1655 (s), 1525 (m), 1490 (s) cm$^{-1}$.

UV [methanol (log $\epsilon$)]: 212 (3.64) nm. $^1$H NMR (CDCl$_3$): $\delta$10.6 (1 H, s), 4.43 (2 H, s), 3.70 (s) and 3.8–3.5 (t) (a total of 5 H), 2.6–2.3 (2 H, t).

(e) 3-Hydroxy-4,5,6,7-tetrahydroisoxazolo[5,4-c]pyridinium bromide (Ia (salt)).

A solution of methyl 3-hydroxy-4,5,6,7-tetrahydroisoxazolo[5, 4-c]-pyridine-6-carboxylate (309 mg; 1.6 mmol) in a solution of hydrogen bromide in glacial acetic acid (3 ml; 43%) was refluxed for 15 minutes. Upon evaporation to dryness in vacuo the residue was treated with the same reagent (3 ml) for further 15 minutes. Evaporation of the reaction mixture to dryness in vacuo and recrystallization (methanol-ether) of the residue gave Ia (salt) (193 mg; 56%) as faintly reddish crystals, m.p. 162–163° C. (decomp.). IR (KBr): 3700–3300 (m), 3070 (s), 3000–2300 (several bands, m-s), 1670 (m), 1580 (m), 1525 (s), 1505 (w) cm$^{-1}$. UV (methanol): <210 nm. $^1$H NMR [D$_2$O (sodium 3-(trimethylsilyl) propanesulfonate was used as an internal standard)]: $\delta$4.77 (ca. 5 H, s), 4.43 (2 H, t, J 1 Hz), 3.7–3.4 (2 H, q, J 6 and 7 Hz), 3.0–2.7 (2 H, t).

(f) 4,5,6,7-Tetrahydroisoxazolo[5,4-c]pyridin-3-ol zwitterion (Ia)

To a solution of 3-hydroxy-4,5,6,7-tetrahydroisoxazolo[5,4-c]pyridinium bromide (77 mg; 0.35 mmol) in water (0.6 ml) was added a solution of triethylamine (39 mg; 0.39 mmol) in ethanol (0.6 ml). The mixture was left at 25° C. for 2 hours. Ia (42 mg; 86%) was isolated as colourless crystals, m.p. 242°–244° C. (decomp.). IR (KBr): 3700–2900 (s), 2900–1900 (several bands, m-s), 1670 (s), 1625 (m) cm$^{-1}$. UV [methanol (log $\epsilon$)]: 212 (3.64) nm. p$K_A$ values (H$_2$O, 25° C.): 4.44±0.03, 8.48±0.04.

EXAMPLE 2

(Reaction scheme II)

Methyl 3-hydroxy-4,5,6,7-tetrahydroisoxazolo[5,4-c]pyridine-6-carboxylate (Va) and methyl 1,4,5,6,7,7a-hexahydro-1-oxoisozazolo[3,4-c]pyridine-5-carboxylate (VIa)

To an iced solution of sodium hydroxide (9.6 g; 0.24 mol) and hydroxylammonium chloride (8.34 g; 0.12 mmol) in water (100 ml) was added with stirring ethyl 1-methoxycarbonyl-3-oxopiperidine-4-carboxylate (22.9 g; 0.1 mol). Upon standing at 5° C. for 5 hours the solution was evaporated to dryness in vacuo. The residue was dissolved in concentrated hydrochloric acid (75 ml) and heated to 70° C. for 10 minutes. The mixture was evaporated in vacuo to the formation of a black residue, which was extracted with three 100 ml portions of chloroform. The combined chloroform phases were dried (Na$_2$SO$_4$) and evaporated in vacuo to the formation of a black semisolid residue. TLC ((silica gel F$_{254}$), eluent: benzene-ethyl acetate-formic acid (25:25:1)) showed the presence of two compounds with $R_F$ values 0.31 and 0.16 corresponding to Va and VIa, respectively. Column chromatography (silica gel: 300 g; eluent: benzene-ethyl acetate-formic acid (30:20:1)) lead to Va and VIa.

EXAMPLE 3

Methyl 3-hydroxy-4,5,6,7-tetrahydro[5,4-c]pyridine-6-carboxylate (Va) (Reaction Scheme I)

A solution of the hydroxamic acid (IXa) (10 g) in perchloric acid (70%; 35 ml) was heated to 60° C. for 30 minutes. Upon cooling, NaOH (40 ml; 28%) was added with stirring and cooling. The mixture was extracted with three 50 ml portions of chloroform. The combined and dried (MgSO$_4$) chloroform phases were filtered and evaporated to dryness in vacuo to form a residue which was dissolved in ethyl acetate (50 ml). Upon standing and cooling, Va was isolated as crystals (6.3 g; 82%). Isolation and washing twice with 30 ml portions of ethyl acetate yielded crystalline Va, m.p. 139°–141° C.

Instead of heating to 60° C. for 30 minutes, the same result may be achieved on standing at ambient temperature for 16 hours.

4,5,6,7-Tetrahydroisoxazolo[5,4-c]pyridine-3-ol zwitterion (Ia)

A solution of methyl 3-hydroxy-4,5,6,7-tetrahydroisoxazolo[5,4-c]pyridine-6-carboxylate (Va) (37 g) in hydrogen bromide in glacial acetic acid (33% HBr, 250 ml) was left for 16 hours at ambient temperature. Evaporation to dryness in vacuo gave the HBr salt of Ia as a yellowish crystalline material, which was dissolved in a mixture of water (100 ml) and ethanol (200 ml). Triethylamine was added until pH 6.5, which caused Ia zwitterion to crystallize. Upon standing for 3 hours at 5° C. and filtration, the precipitate was washed on the filter with a mixture of water (25 ml) and ethanol (50 ml) to give the zwitterion (26 g; 95%) as a white crystalline material, m.p. 242°–244° C. (decomp.).

I claim:
1. A compound of the formula

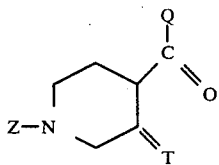

wherein Z is acetyl; a group of the formula

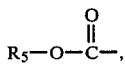

in which $R_5$ is $C_{1-8}$ alkyl, phenyl, phenyl substituted in the 4-position with halogen, lower-alkoxy, or lower-alkyl, or phenyl-lower-alkyl in which the phenyl group may be substituted in the 4-position with halogen, lower-alkoxy, or lower-alkyl; trityl; or formyl; T is ethylenedioxy, and Q is halogen lower-alkoxy; lower-alkyl or lower-alkoxy in any of the foregoing containing one through four carbon atoms.

2. A compound of the formula

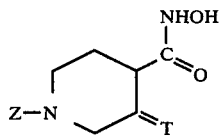

wherein Z is acetyl; a group of the formula

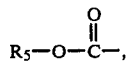

in which $R_5$ is $C_{1-8}$ alkyl, phenyl, phenyl substituted in the 4-position with halogen, lower-alkoxy, or lower-alkyl, or phenyl-lower-alkyl in which the phenyl group may be substituted in the 4-position with halogen, lower-alkoxy, or lower-alkyl; trityl; or formyl; and wherein T is alkylenedioxy lower-alkyl or lower-alkoxy in any of the foregoing containing one through four carbon atoms.

3. A compound of claim 1 wherein Q is ethoxy.

4. A compound of claim 2, wherein T is ethylene dioxy.

5. A compound of the formula

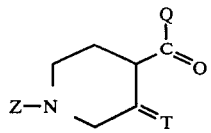

wherein Z is hydrogen, T is ethylenedioxy and Q is halogen or lower-alkoxy; lower-alkoxy containing one through four carbon atoms.

6. A compound of the formula

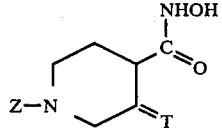

wherein Z is hydrogen and wherein T is ethylenedioxy.

7. A compound of claim 3, wherein Z is methoxycarbonyl.

8. A compound of claim 2, wherein T is ethylene dioxy and Z is methoxycarbonyl.

* * * * *

UNITED STATES PATENT AND TRADEMARK OFFICE
CERTIFICATE OF CORRECTION

PATENT NO. : 4,301,287
DATED : November 17, 1981
INVENTOR(S) : Povl Krogsgaard-Larsen It is certified that error appears in the above—identified patent and that said Letters Patent is hereby corrected as shown below:

On the title Item /75/, "Blovstrod, Denmark" should read --Allerød, Blovstrød, Denmark--.
[57] ABSTRACT, righthand column, second line after third group of
   formulas; "oxy" should read -- oxo --
Col. 3, line 28; "canounds" should read -- compounds --
Col. 5, line 40; "GABADOPAMINE" should read -- GABA-DOPAMINE --
Col. 7, last formula, left of the arrow; "O,HBR" should read -- O,HBr --
   (also shown below)

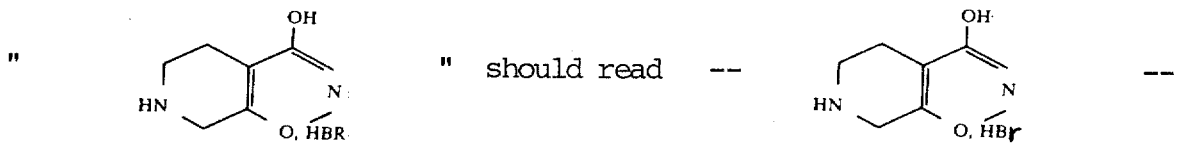

Col. 13, line 11; "(1:1):" should read -- (1:1)]: --
Col. 15, line 21; insert a comma -- , -- after "halogen"

Signed and Sealed this

Eighteenth Day of May 1982

[SEAL]

Attest:

Attesting Officer

GERALD J. MOSSINGHOFF
Commissioner of Patents and Trademarks